United States Patent [19]
Takashima et al.

[11] Patent Number: 5,863,866
[45] Date of Patent: Jan. 26, 1999

[54] PYRAZOLE DERIVATIVES

[75] Inventors: Yoriyuki Takashima, Sodegaura; Ichiro Nasuno, Ichihara; Hiroshi Yamamoto, Sodegaura, all of Japan

[73] Assignee: Idemitsu Kosan Co., Ltd., Tokyo, Japan

[21] Appl. No.: 894,752

[22] PCT Filed: Mar. 28, 1996

[86] PCT No.: PCT/JP96/00810

§ 371 Date: Jan. 6, 1998

§ 102(e) Date: Jan. 6, 1998

[87] PCT Pub. No.: WO96/31507

PCT Pub. Date: Oct. 10, 1996

[30] Foreign Application Priority Data

Apr. 5, 1995 [JP] Japan ........................ 7-80059

[51] Int. Cl.$^6$ .................... C07D 409/10; A01N 43/56
[52] U.S. Cl. ........................ 504/282; 548/364.4
[58] Field of Search ................ 504/282; 548/364.4

[56] References Cited

U.S. PATENT DOCUMENTS 5,468,722 11/1995 Shibata et al. ............ 504/282

FOREIGN PATENT DOCUMENTS 7-309869 11/1995 Japan.
WO 93/18031 9/1993 WIPO.
WO 96/00008 1/1996 WIPO.

*Primary Examiner*—S. Mark Clardy
*Assistant Examiner*—Sabiha N. Qazi
*Attorney, Agent, or Firm*—Frishauf, Holtz, Goodman, Langer & Chick, P.C.

[57] ABSTRACT

Novel pyrazole derivatives in which a thiochroman ring bonds to a pyrazole through carbonyl group and R1 is haloalkyl group in formula (I) exhibit excellent selectivity between crops and weeds in foliar treatment and soil treatment.

24 Claims, No Drawings

PYRAZOLE DERIVATIVES

This application has been filed under 35 USC 371 as national stage application of PCT/JP 96/00810.

TECHNICAL FIELD

The present invention relates to pyrazole derivatives and herbicides containing the pyrazole derivatives as active ingredients.

TECHNICAL BACKGROUND

It is indispensable to use a herbicide for protecting, and increasing the yields of, useful crops such as rice, wheat, barley, corn, soybean, cotton, beet and the like. In recent years in particular, there are desired selective herbicides which cause no phytotoxicity on the useful crops but selectively control weeds alone by foliar treatment of the crops and the weeds at the same time in a cultivated field where the useful crops and weeds are concurrently present.

During the planting time of corn, etc., triazine-based herbicides such as atrazine and acid anilide-based herbicides such as alachlor and metolachlor have been conventionally used as soil treating chemical. However, these herbicides require high dosage and are therefore causing environmental problems such as pollution of ground water.

In recent years, further, "non-tilled cropping" intended for soil conservation is promoted. "Non-tilled cropping" is a method of cultivating crops without plowing, and is against usual tilled cropping. In tilled cropping, fertile surface soil which is tilled (plowed) is washed away by rain, etc., which is not only a great farming problem but also a problem which leads to a kind of desertification. On the other hand, in non-tilled cropping, there is no problem of surface soil being washed away. However, without tilling, soil is hardened so that a chemical is scarcely infiltrated into the soil, and the effect of the chemical on soil treatment decreases. In the non-tilled cropping, therefore, there are demanded herbicides which have high herbicidal efficacy at a low dosage in soil treatment and which can be used as a single chemical for foliar treatment as well.

International Laid-open Patent Publication No. WO93/18031 discloses herbicidally active pyrazole derivatives having a thiochroman ring, represented by the following formula,

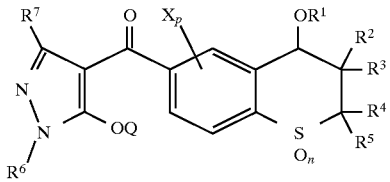

wherein $R^1$ is a $C_1$–$C_6$ alkyl group. Explanations of the other symbols are omitted.

Typical compound (A) of the above International Laid-open Patent Publication (Compound No. 66 in the Publication) has the following structural formula.

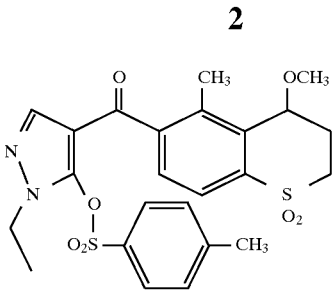

The above compound (A) shows excellent selectively between crops and weeds without damaging cultivated crops when used for the treatment of corn, wheat, barley, etc., at the stage of 1~2 leaves. However, when the foliar treatment is carried out at the stage of 3~4 leaves, the safety to the crops is not fully satisfactory.

DISCLOSURE OF THE INVENTION

It is a first object of the present invention to provide a novel pyrazole derivative which has remarkably high herbicidal activity against a broad range of weeds at a low dosage, exhibits high safety to useful crops such as wheat, barley, corn, soybean, cotton, beet, rice, etc., and exhibits excellent selectivity between crops and weeds, in both foliar treatment and soil treatment.

Further, it is a second object of the present invention to provide a herbicide containing the above novel pyrazole derivative as an active ingredient.

The present inventors have made diligent studies for creating novel pyrazole derivatives which can achieve the above objects, and as a result have found the following. Compounds obtained by replacing the $C_1$–$C_6$ alkyl group as $R^1$ in the structural formula of the pyrazole derivative of the above International Laid-open Patent Publication by a $C_1$–$C_6$ haloalkyl group having at least one halogen atom exhibits excellent selectivity between crops and weeds. The present invention has been completed on the basis of the above finding.

That is, the first object of the present invention is achieved by a pyrazole derivative of the formula (I),

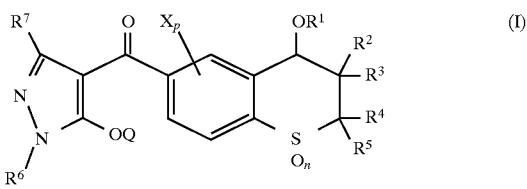

wherein:

$R^1$ is a $C_1$–$C_6$ haloalkyl group having at least one halogen atom;

each of $R^2$, $R^3$, $R^4$ and $R^5$ is independently a hydrogen atom or a $C_1$–$C_4$ alkyl group;

$R^6$ is a $C_1$–$C_4$ alkyl group, $R^7$ is a hydrogen atom or a $C_1$–$C_4$ alkyl group, X is a $C_1$–$C_4$ alkyl group or a halogen atom, each of p and n is independently an integer of 0, 1 or 2; and Q is a hydrogen atom or a group of -A-B, in which A is —$SO_2$—, —$(CH_2)_k$-CO— or —$CR^8R^9$- in which k is an integer of 0 or 1 to 3 and each of $R^8$ and $R^9$ is independently a hydrogen atom or a $C_1$–$C_4$ alkyl group; and B is a $C_1$~$C_{12}$ alkyl group, a $C_3$~$C_{12}$ cycloalkyl group or a group of —Ph-$Y_m$ in which Ph is a phenyl group, Y substituted on the Ph is a $C_1$~$C_4$ alkyl group, a $C_1$~$C_4$ alkoxy group, a $C_1$~$C_4$ haloalkyl group having at least one halogen atom, a nitro group or a halogen atom, and m is an integer of 0, 1 or 2.

Further, the second object of the present invention is achieved by a herbicide containing the pyrazole derivative of the above formula (I) as an active ingredient.

PREFERRED EMBODIMENTS OF THE INVENTION

The novel pyrazole derivative which achieves the first object of the present invention has the structure of the following formula (I).

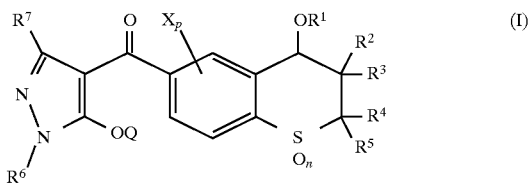

In the above formula (I), $R^1$ is a $C_1$~$C_6$ haloalkyl group having at least one halogen atom. The $C_1$–$C_6$ alkyl group forming the skeleton of $R^1$ includes methyl, ethyl, propyl, butyl, pentyl and hexyl. When this alkyl group has at least 3 carbon atoms, the alkyl group may be linear or branched. The $C_1$–$C_6$ alkyl group is preferably methyl or ethyl. The halogen atom substituted on the $C_1$–$C_6$ alkyl group forming the skeleton of $R^1$ includes chlorine, fluorine, bromine and iodine atoms, and chlorine and fluorine atoms are preferred. Halogen atom(s) may be substituted for any hydrogen atom(s) of the $C_1$–$C_6$ alkyl group of $R^1$. The number of the halogen atom(s) substituted on the $C_1$–$C_6$ alkyl group is preferably 1 to 7, particularly preferably 1.

Examples of the haloalkyl group as $R^1$ include -Z-$CH_2$— (Z is a halogen atom and will be used in this sense hereinafter; one halogen atom is substituted), Z-$CH_2CH_2$— (one halogen atom is substituted), $(CZ_3)_2$CH— (six halogen atoms are substituted), $Z(CZ_2)_q(CH_2)_s$— (q is an integer of 1 to 3 and s is an integer of 0 to 5; 3 to 7 halogen atoms are substituted), and H $(CZ_2)_r(CH_2)_s$— (r is an integer of 1 to 5 and s is an integer of 0 to 5; 2 to 10 halogen atoms are substituted).

$R^1$ is preferably a linear or branched $C_1$~$C_4$ haloalkyl group, such as chloromethyl, fluoromethyl, 2-chloroethyl or 2-fluoroethyl, particularly preferably 2-chloroethyl or 2-fluoroethyl.

In the above formula (I), each of $R^2$, $R^3$, $R^4$ and $R^5$ is independently a hydrogen atom or a $C_1$~$C_4$ alkyl group. Examples of the $C_1$~$C_4$ alkyl group include methyl, ethyl, propyl and butyl, and the propyl and butyl may be linear or branched.

Specific examples of each of $R^2$, $R^3$, $R^4$ and $R^5$ preferably include a hydrogen atom and methyl, and particularly preferably, each of $R^2$, $R^3$, $R^4$ and $R^5$ is independently a hydrogen atom.

In the above formula (I), $R^6$ is a $C_1$~$C_4$ alkyl group and $R^7$ is a hydrogen atom or a $C_1$~$C_4$ alkyl group. Specific examples of these $C_1$~$C_4$ alkyl groups include those described in the explanation of the above $R^2$, $R^3$, $R^4$ and $R^5$.

Specifically, $R^6$ is preferably methyl or ethyl, particularly preferably ethyl.

Specifically, $R^7$ is preferably a hydrogen atom or methyl, particularly preferably a hydrogen atom.

In the above formula (I), X is a $C_1$~$C_4$ alkyl group or a halogen atom. Specific examples of the $C_1$~$C_4$ alkyl group and the halogen atom include those described in the above explanation.

Specificaly, X is preferably methyl, a chlorine atom or a fluorine atom, particularly preferably methyl. X(s) can be substituted on the any site(s) of 5-, 7- and 8-positions on the thiochroman ring, and is/are preferably substituted on the 5-position and/or the 8-position.

In the above formula (I), p is the number of substituted X(s), and it is an integer of 0, 1 or 2, preferably 1 or 2, particularly preferably 2.

In the above formula (I), n is the number of oxygen atom(s) bonding to the sulfur atom of the thiochroman ring, and it is an integer of 0, 1 or 2. That is, when n is 0, a sulfide is represented, when n is 1, a sulfoxide is represented, and when n is 2, a sulfone is represented. Preferably, n is 2, or a sulfone is represented.

In the above formula (I), Q is a hydrogen atom or a group of -A-B.

When Q is a group of -A-B, A is —$SO_2$—, —$(CH_2)_k$-CO— or —$CR^8R^9$-. In the formulae for A, k is an integer of 0 or 1 to 3 and each of $R^8$ and $R^9$ is independently a hydrogen atom or a $C_1$~$C_4$ alkyl group.

Specific examples of the —$(CH_2)_k$-CO— as A include —CO— (k=0), —$(CH_2)$CO— (k=1), —$(CH_2)_2$CO— (k=2) and —$(CH_2)_3$CO— (k=3). the —$(CH_2)_k$-CO— is preferably —CO— (k=0) or —$(CH_2)$CO— (k=1).

Specific examples of the —$CR^8R^9$- as A include —$CH_2$—, —$CH(CH_3)$—, —$C(CH_3)_2$—, —$CH(C_2H_5)$— and —$C(C_2H_5)_2$. The —$CR^8R^9$— is preferably —$CH_2$— or —$CH(CH_3)$—.

A is preferably —$SO_2$— or —CO— (k=0).

When Q is a group of -A-B, B is a $C_1$~$C_{12}$ alkyl group, a $C_3$~$C_{12}$ cycloalkyl group or a group of -Ph-$Y_m$.

Specific examples of the $C_1$~$C_{12}$ alkyl group as B includes those described in the explanation of the above $C_1$~$C_4$ alkyl group as well as pentyl, hexyl, heptyl, octyl, nonyl, decanyl, undecanyl and dodecanyl. The alkyl group having at least 3 carbon atoms may be linear or branched.

Specific examples of the $C_3$~$C_{12}$ cycloalkyl group as B include cyclopropyl, cyclobutyl, cyclopentyl, cyclohexyl, cycloheptyl, cyclooctyl, cyclononyl and cyclodecyl. The number of carbon atoms of the cycloalkyl group is 3 to 12 as described above, while the cycloalkyl group having at least 4 carbon atoms may be a cycloalkyl group having an alkyl group substituted on its ring. For example, the cycloalkyl group having 4 carbon atoms may be methyl-substituted cyclopropyl.

When B is a group of -Ph-$Y_m$, Y is a $C_1$~$C_4$ alkyl group, a $C_1$~$C_4$ alkoxy group, a $C_1$~$C_4$ haloalkyl group having at least one halogen atom, a nitro group or a halogen atom, and m is an integer of 0, 1 or 2. That m is 0 means that Y is not substituted on Ph (phenyl group), i.e., no substituent on the phenyl group. When m is an integer of 1 or 2, Y is substituted on one site of the 2-, 3-, 4-, 5- or 6-positions on Ph (phenyl group) or Ys are substituted on two sites of the 2-, 3-, 4-, 5- or 6-positions on Ph (phenyl group).

When B is a group of -Ph-$Y_m$ and when Y is a $C_1$~$C_4$ alkyl group, specific examples of the $C_1$~$C_4$ alkyl group include those described in the above explanation. When Y is a $C_1$~$C_4$ alkoxy group, specific examples of the $C_1$~$C_4$ alkoxy group include methoxy, ethoxy, propoxy and butoxy, and the propoxy and butoxy may be linear or branched. When Y is a $C_1$~$C_4$ haloalkyl group having at least one halogen atom, specific examples of the $C_1$~$C_4$ haloalkyl group having at least one halogen atom include those described in the above explanation of $R^1$. The halogen atom includes fluorine, chlorine, bromine and iodine atoms.

B is preferably a $C_1$~$C_4$ alkyl group, a $C_3$–$C_8$ cycloalkyl group or a group of -Ph-$Y_m$, particularly preferably ethyl, n-propyl, cyclohexyl, phenyl (m=0 in the group of -Ph-$Y_m$), or p-toluyl (Y=4-methyl and m=1 in the group of -Ph-$Y_m$).

Q is preferably a hydrogen atom or a group of -A-B in which the combination of A and B is as follows.

That is, preferably, A is —$SO_2$— and B is a $C_1$~$C_4$ alkyl group or a group of -Ph-$Y_m$. Particularly preferably, A is —$SO_2$— and B is ethyl, n-propyl o p-toluyl (Y=4-methyl and m=1 in the group of -Ph-$Y_m$). Further, preferably, A is —$(CH_2)_k$— CO— and B is a $C_3$–$C_8$ cycloalkyl group or the group of -Ph-$Y_m$. Particularly preferably, A is —CO— (k=0 in —$(CH_2)_k$-CO—) or —$CH_2$CO— (k=1 in —$(CH_2)_k$-CO—) and B is phenyl (m=0 in the group of -Ph-$Y_m$) or cyclohexyl.

The pyrazole derivative of the formula (I) in which Q is a hydrogen atom, i.e., a compound of the formula (Ia),

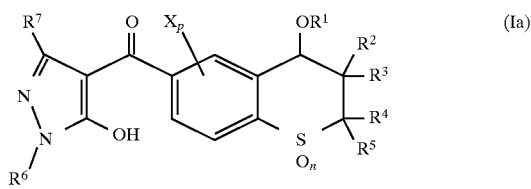

(In the formula, each symbol is as defined in the formula (I)) can have the following three structures of the formulae (Ib), (Ic) and (Id) due to tautomerism, and the pyrazole derivative of the present invention includes all of these compounds and mixtures of these.

The above base can be selected from known bases without any limitation, and examples of the base include organic bases such as amines and anilines and inorganic bases such as sodium compounds and potassium compounds. Examples of the amines include monoalkylamine, dialkylamine and trialkylamine. Alkyl groups of the alkylamines are generally $C_1$~$C_4$ alkyl groups. Examples of the anilines include aniline, monoalkylaniline and dialkylaniline. Alkyl groups of the alkylanilines are generally $C_1$~$C_4$ alkyl groups. Examples of the sodium compounds include sodium hydroxide and sodium carbonate. Examples of the potassium compounds include potassium hydroxide and potassium carbonate.

Further, the pyrazole derivative of the formula (I) has asymmetric carbon, and various isomers are therefore present. The pyrazole derivative of the present invention includes all of these isomers and mixtures of these.

The herbicide of the present invention contains the novel pyrazole derivative of the formula (1) and/or the salt thereof, provided by the present invention, as active ingredient. These compounds are used by mixing them with a liquid carrier such as a solvent or a solid carrier such as a mineral fine powder and preparing the resultant mixtures in the form of a wettable powder, an emulsifiable concentrate, a dust or granules. These compounds can be imparted with emulsifiability, dispersibility or spreadability by adding a surfactant when the above preparations are formed.

When the herbicide of the present invention is used in the form of a wettable powder, generally, 10 to 55% by weight of the pyrazole derivative and/or the salt thereof, provided by the present invention, 40 to 88% by weight of a solid carrier and 2 to 5% by weight of a surfactant are mixed to prepare a composition, and the composition can be used. When the herbicide of the present invention is used in the form of an emulsifiable concentrate, generally, the emulsifiable concentrate can be prepared by mixing 20 to 50% by

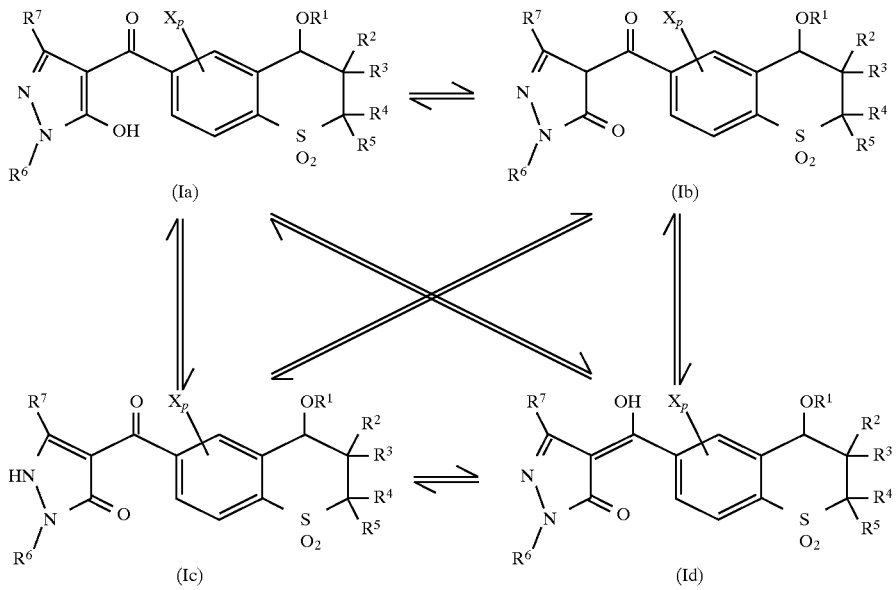

In the above formulae, each symbol is as defined in the formula (I).

The pyrazole derivative of the formula (Ia) is an acidic substance, and can be easily converted to a salt by treating it with a base. This salt is also included in the pyrazole derivative of the present invention.

weight of the pyrazole derivative and/or the salt thereof, provided by the present invention, 35 to 75% by weight of a solvent and 5 to 15% by weight of a surfactant.

When the herbicide of the present invention is used in the form of a dust, generally, the dust can be prepared by mixing 1 to 15% by weight of the pyrazole derivative and/or the salt thereof, provided by the present invention, 80 to 97% by weight of a solid carrier and 2 to 5% by weight of a surfactant. Further, when the herbicide of the present invention is used in the form of granules, the granules can be prepared by mixing 1 to 15% by weight of the pyrazole derivative or the salt thereof, provided by the present invention, 80 to 97% by weight of a sold carrier and 2 to 5% by weight of a surfactant. The above solid carrier is selected from mineral powders. Examples of the mineral powders include oxides such as diatomaceous earth and slaked lime, phosphates such as apatite, sulfates such as gypsum and silicates such as talc, pyrophyllite, clay, kaolin, bentonite, acidic terra alba, white carbon, powdered quartz and powdered silica.

The solvent is selected from organic solvents. Specific examples of the solvent include aromatic hydrocarbons such as benzene, toluene and xylene, chlorinated hydrocarbons such as o-chlorotoluene, trichloroethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, diethyl ether and methyl ethyl ether, esters such as isopropyl acetate, benzyl acetate and methyl phthalate, amides such as dimethylformamide, and mixtures of these.

The surfactant is selected from anionic surfactants, nonionic surfactants, cationic surfactants and amphoteric surfactants (such as amino acid and betaine).

Together with the pyrazole derivative of the formula (I) and/or the salt thereof, the herbicide of the present invention may contain other herbicidally active ingredient as required. The other herbicidally active ingredient cab be properly selected from known herbicides such as phenoxy-based, diphenyl ether-based, triazine-based, urea-based, carbamate-based, thiol carbamate-based, acid anilide-based, pyrazole-based, phosphoric acid-based, sulfonyl urea-based and oxadiazone-based herbicides.

Further, the herbicide of the present invention may contain an insecticide, a fungicide, a plant growth regulator and a fertilizer as required.

The compound of the present invention can be used as a herbicide for upland soil by any method of soil treatment, treatment by mixing it with soil, and foliar treatment. The cropland weeds which the compound of the present invention is used for controlling include broad-leaved weeds such as solanaceous weeds typified by black nightshade (*Solanum nigrum*) and jimsonweed (*Datura stramonium*); malvaceous weeds typified by velvetleaf (*Abutilon theophrasti*) and pricky sida (*Side spinosa*); convolvulaceous weeds typified by moring-glories (*Ipomoea spps.*) such as tall morningglory (*Ipomoea purpurea*) and hedge bindweeds (*Calystegia spps.*); amaranthaceous weeds typified by livid amaranth (*Amaranthus lividus*); compositae weeds typified by cocklebur (*Xanthium strumarium*), common ragweed (*Ambrosia artemisiaefolia*), sunflower (*Helianthus annus*), hairy galinsoga (*Galinsoga ciliata*), Canadathistle (*Cirsiumarvense*), groundsel (*Senecio vulgaris*) and annual fleabane (*Erigeron annus*); brass icaceous weeds (cruciferae) typified by yellow cress (*Rorippa indica*), wild mustard (*Sinapis arvensis*) and shepherdspurse (*Capsella bursa-pastoris*); polygonaceaus weeds typified by wild buckwheat (*Polygonum convolvulus*); portulacaceaus weeds typified by common purslane (*Portulaca oleracea*); chenopodiaceous weeds typified by common lambsquaters (*Chenopodium album*), fig-leaved goosefoot (*Chenopodium ficifolium*) and kochia (*Kochia scoparia*); caryophyllaceous weeds typified by common chickweed (*Stellaria media*); scrophularaceous weeds typified by persian speedwell (*Veronica persica*); commelinaceous weeds typified by Asiatic dayfower (*Commelina communis*); labiate weeds typified by henbit (*Laminum amplexicaule*) and purple deadnettle (*Lamium purpureum*); euphorbiaceous weeds typified by milk purslane (*Euphorbia supina*) and spotted spurge (*Euphorbia maculata*); rubiaceous weeds typified by bedstraw (*Galium spurium*), cleavers (*Galium aparine*) and madder (*Rubia akane*); violaceous weeds violet (*Viola arvensis*); and leguminous weeds typified by hemp sesbania (*Sesbania exaltata*) and sicklepod (*Cassia obtusifolia*); graminaceous weeds typified by sorghum (*Sorghum bicolor*), fall panicum (*Panicum dichotomiflorum*), johnsongrass (*Sorghum halepense*), barnyardgrass (*Echinocholoa crus-galli*), henry crabgrass (*Digitaria adscendens*), wildoat (*Avena fatua*), goosegrass (*Eleusine indica*), green foxtail (*Setaria viridis*) and water foxtail (*Alopecurus aequalis*); and cyperaceous weeds typified by purple nutsedge (*Cyperus rotundus, Cyperus esculentus*).

Further, the compound of the present invention can be also used for any one of soil treatment and foliar treatment under submergence as a herbicide for paddy land. Examples of paddy weeds include alismataceous weeds typified by oriental waterplantain (*Alisma canaliculatum*), arrowhead (*Sagittaria trifolia*) and *Sagittaria pygmaea*; cyperaceous weeds typified by umbrella plant (*Cyperus difformis*), *Cyperus serotinus*, bulrush (*Scirpus juncoides*) and water chestnut (*Eleocharis kuroguwai*); scrothulariaceous weeds typified by common falsepimpernel (*Lindenia pyxidaria*); potenderiaceous weeds typified by monochoria (*Monochoria Vaginalis*); potamogetonaceous weeds typified by largeleaf pondweed (*Potamogeton distinctus*); lythraceous weeds typified by toothcup (*Rotala indica*); and graminaceous weeds typified by barnyardgrass (*Echinochloa crus-galli*).

Further, the compound of the present invention can be applied to non-agricultural fields such as sports grounds, vacant land, railroad sides, etc., in addition to upland field, paddy land and orchards.

The novel pyrazole derivative of the formula (I) can be produced by a number of methods, for example, by the following method.

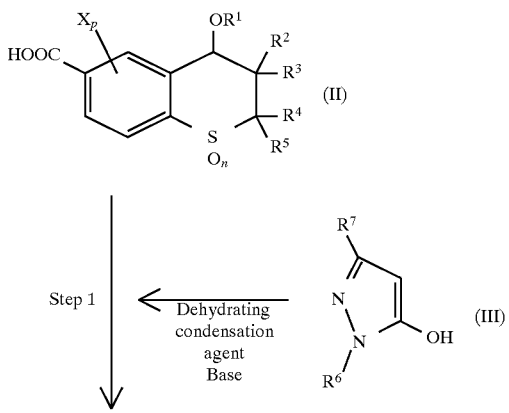

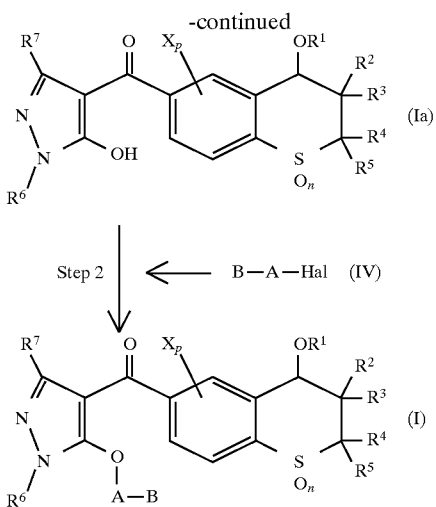

In the above reaction scheme, symbols are as defined in the formula (I) and Hal is a halogen atom.

The pyrazole derivative of the formula (I) in which Q is a hydrogen atom, i.e., the pyrazole derivative of the formula (Ia), provided by the present invention, can be obtained by reacting a carboxylic acid derivative of the formula (II) with a pyrazole compound of the formula (III) in an inert solvent in the presence of a dehydrating condensation agent and a base (step 1).

Further, the pyrazole derivative of the formula (I) in which Q is a group of -A-B, provided by the present invention, can be obtained by reacting the pyrazole derivative of the formula (Ia) with a halogen compound of the formula (IV) in an inert solvent (step 2).

Each of the above steps will be explained below.

Step 1

The amount of the pyrazole compound of the formula (III) per mole of the carboxylic acid derivative of the formula (II) is preferably 1.0 to 3.0 mol.

The dehydrating condensation agent used in the present invention includes N,N-dicyclohexylcarbodiimide (DCC), 1,1-carbonyldiimidazole (CDI) and 1-(3-dimethylaminopropyl)-3-ethylcarbodiimide (EDC). DCC is preferred. The amount of the dehydrating condensation agent per mole of the carboxylic acid derivative of the formula (II) is preferably 1.0 to 1.5 mol.

Although not specially limited, the base used in the present invention is preferably selected from potassium carbonate and sodium carbonate. The amount of the base per mole of the carboxylic acid derivative of the formula (II) is preferably 0.5 to 2.0 mol.

The solvent used in the above reaction is not specially limited so long as it is inert to the reaction. The solvent is selected from acetonitrile, t-amyl alcohol, t-butyl alcohol and i-propyl alcohol. t-Amyl alcohol is preferred.

The reaction temperature can be in the range of from 0° C. to the boiling point of the solvent, and a temperature around 80° C. is preferred. The reaction time is 1 to 48 hours, generally about 8 hours.

After the completion of the reaction, the solvent is distilled off under reduced pressure, a weak alkaline aqueous solution of sodium carbonate or potassium carbonate is added to the residue to dissolve the residue therein, and an insoluble is removed by filtration. An aqueous layer is washed with an organic solvent such as ethyl acetate, chloroform, dichloromethane or dichloroethane, and then acidified by adding diluted hydrochloric acid, diluted sulfuric acid and the like. A formed solid or oily substance is recovered by filtration or extracted with an organic solvent such as ethyl acetate, chloroform, dichloromethane or dichloroethane, whereby the intended pyrazole derivative of the formula (Ia) is obtained.

Step 2

The amount of the halogen compound of the formula (IV) per mole of the pyrazole derivative of the formula (Ia) is preferably 1 to 3 mol.

For trapping hydrogen halide formed as a byproduct in the reaction, it is preferred to use a base such as sodium carbonate, potassium carbonate, triethylamine or pyridine in at least an equimolar amount based on the amount of the pyrazole derivative of the formula (Ia).

The solvent used in the reaction is not specially limited so long as it is inert to the reaction, while it is selected from aromatic hydrocarbons such as benzene and toluene, ether compounds such as diethyl ether, ketone compounds such as methyl ethyl ketone and halogenated hydrocarbons such as chloroform or dichloromethane. Dichloromethane is preferred. Further, a two-phase solvent consisting of the above solvent and water may be used. In this case, a more favorable result can be obtained by adding a phase transfer catalyst to the reaction system, such as crown ether or benzyltriethylammonium chloride.

The reaction temperature is preferably in the range of from room temperature to the boiling point of the solvent. The reaction time is 0.5 to 48 hours, while the reaction is generally completed in 0.5 to 3 hours.

After the completion of the reaction, a weak alkaline aqueous solution of potassium carbonate, sodium carbonate or sodium hydrogencarbonate and an organic solvent such as diethyl ether, dichloromethane, chloroform, dichloroethane or ethyl acetate are added to the reaction mixture, and the mixture is separated into two phases, an organic layer is dried, and then the solvent is distilled off under reduced pressure. The resultant residue is recrystallized or purified by column chromatography as required, to obtain the pyrazole derivative of the present invention, i.e., the pyrazole derivative of the formula (I) in which Q is a group of -A-B as an end product.

The pyrazole compound of the formula (III) used as a reaction reagent in the above method can be synthesized by the method disclosed, for example, in JP-A-61-257974.

Further, the carboxylic acid derivative of the formula (II) used as the other reaction reagent in the above method can be prepared by various methods. Some of the methods are as follows.

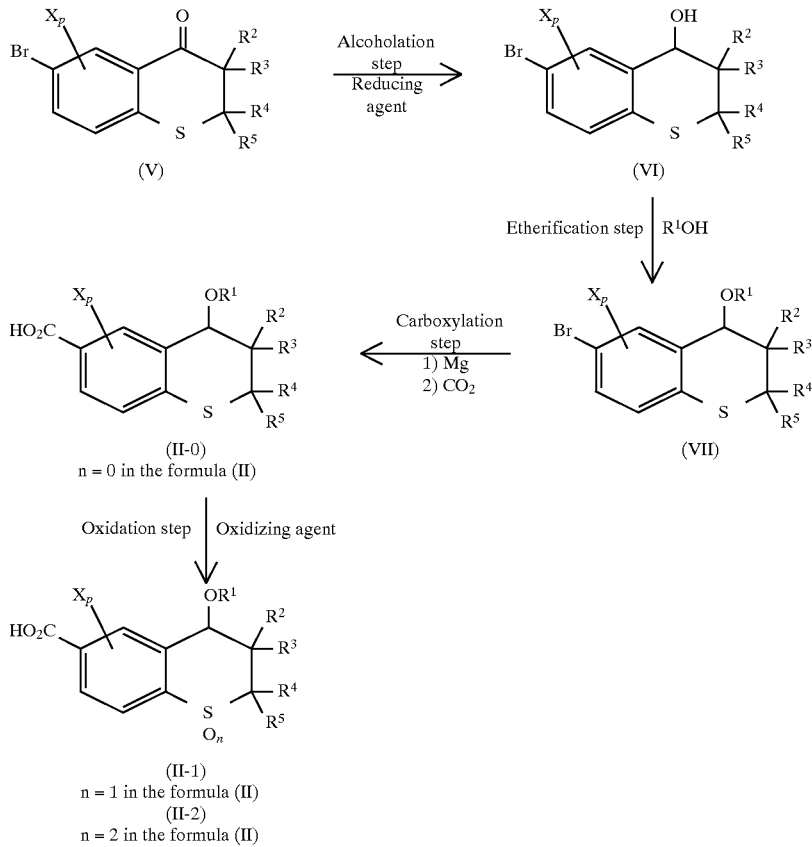
wherein symbols are as defined in the formula (I).
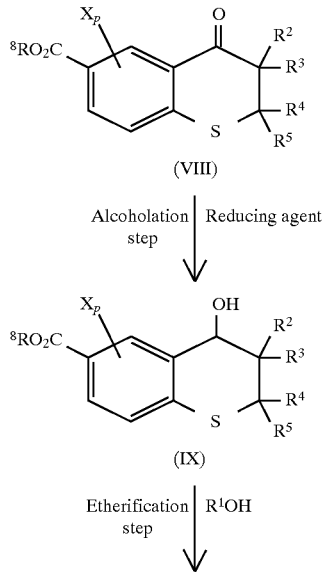

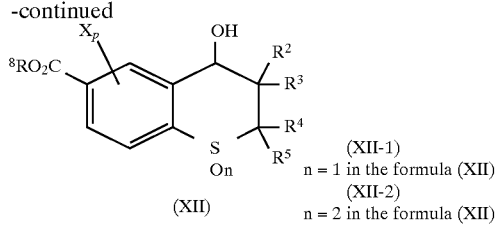
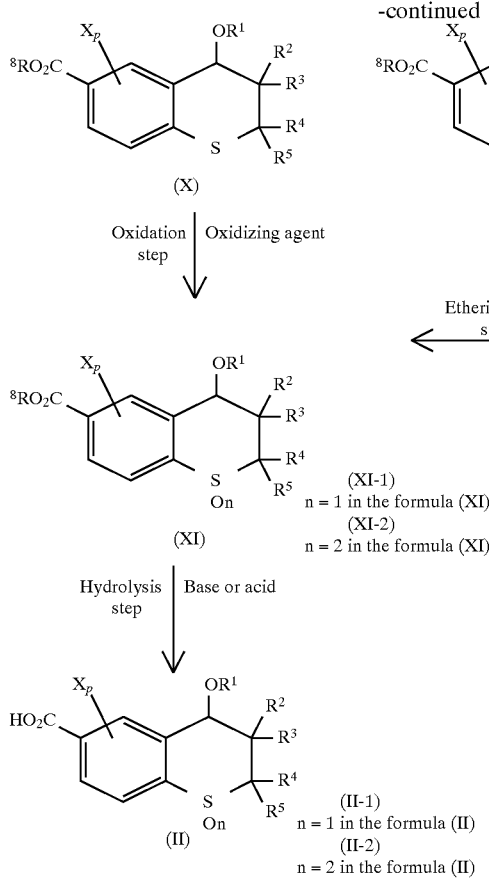

wherein symbols are as defined in the formula (I), and $R^8$ is hydrogen, a $C_1$–$C_4$ alkyl group or a $C_1$–$C_6$ haloalkyl group.

Each step of the above method(s) will be explained below.

Alcoholation step

In a reaction in this step, a ketone of the formula (V) or (VIII) is reduced to form an alcohol of the formula (VI) or (IX).

The ketone of the formula (V) can be prepared by various methods including the method disclosed in International Laid-open Patent Publication No. WO88/06155.

The reducing agent used in the above reaction can be selected from various reducing agents, and for example, sodium borohydride is preferred.

The reaction temperature is generally −20° C. to 50° C.

Etherification step

In a reaction in this step, an alcohol of the formula (VI), (IX) or (XII) and an alcohol of the formula of $R^1OH$ are dehydratively condensed in the presence of a catalyst and a solvent, to form an ether of the formula (VII), (X) or (XI). The carboxylic acid of the formula (XII) or (IX) is concurrently esterified in some cases.

The catalyst used in the above reaction is selected from acid catalysts such as sulfuric acid, aromatic sulfonic acid, sulfonic acid halide, boron trifluoride and aluminum chloride. The catalyst serves for a smooth reaction.

The solvent used in the above reaction is selected from aromatic hydrocarbons such as benzene, toluene and xylene and halogenated hydrocarbons such as 1,2-dichloroethane and carbon tetrachloride. Further, the alcohol of the formula of $R^1OH$ may be used in an excess amount to co-use it as a solvent.

Carboxylation step

In a reaction in this step, the compound of the formula (VII) is reacted with magnesium to form a Grignard reagent, and the Grignard reagent is reacted with carbon dioxide to obtain a carboxylic acid derivative of the formula (II-0) (n=0, sulfide).

The solvent used in the above reaction is preferably selected from diethyl ether and tetrahydrofuran.

The reaction temperature is generally 0° to 50° C.

Oxidation step

In this step, the sulfur atom of the carboxylic acid derivative of the formula (II-0) or (X) is oxidized to obtain a carboxylic acid derivative of the formula (II-1) or (II-2) or a carboxylic acid derivative of the formula (XI-1) or (XI-2) (sulfoxide when n=1, sulfone when n=2).

The oxidizing agent used in the above step can be selected from various oxidizing agent, while hydrogen peroxide is particularly preferred.

The solvent used in the above step can be selected from various solvents, while acetic acid is particularly preferred.

For obtaining the compound of the formula (II) in which n=1 (sulfoxide), the amount of the oxidizing agent is 1 equivalent weight based on the carboxylic acid of the formula (II-), and the reaction is carried out at 0° to 30° C. For obtaining the compound of the formula (II) in which n=2 (sulfone), the amount of the oxidizing agent is at least 2 equivalent weight based on the carboxylic acid of the formula (II-), and the reaction is carried out at 50° to 100° C.

The above explanation is also true of the compounds of the formula (X).

Hydrolysis step

In a reaction in this step, the compound of the formula (XI) is reacted with a base or an acid to hydrolyze the ester, whereby a compound of the formula (II) is obtained.

The base used in the above reaction preferably selected from sodium hydroxide and potassium hydroxide. The acid used in the above reaction is preferably selected from hydrochloric acid and sulfuric acid.

The amount of the base or the acid is 1 to 5 mol per mole of the ester.

The solvent used in the above reaction is preferably selected from methanol, ethanol and ethylene glycol.

The reaction temperature is generally 0° to 100° C.

The present invention will be more specifically explained with reference to Referential Preparation Examples, Preparation Examples and Herbicide Examples hereinafter, while the present invention shall not be limited thereto.

(REFERENTIAL PREPARATION EXAMPLE 1)

SYNTHESIS OF CARBOXYLIC ACID DERIVATIVE OF THE FORMULA (II)

(1) Alcoholation step 100 ml of methanol and 30 ml of dichloromethane were added to 10 g (36.9 mmol) of 5,8-dimehyl-6-bromothiochroman-4-one. While the mixture was maintained at a temperature not exceeding 0° C. with a sodium chloride aqueous solution and an ice bath, 0.70 g (18.4 mmol) of sodium borohydride as a reducing agent was gradually added. The mixture was allowed to react at room temperature for 3 hours, and then the reaction mixture was poured into a 5% hydrochloric acid aqueous solution and extracted with dichloromethane. The resultant dichloromethane layer was dried over anhydrous sodium sulfate and concentrated to give 9.2 g (yield 91%) of 5,8-dimethyl-4-hydroxy-6-bromothiochroman (corresponding to compound of the formula (VI)).

(2) Etherification step

17 Grams of 2-fluoroethanol and 3 drops of concentrated sulfuric acid were added to 9.2 g (33.7 mmol) of the 5,8-dimethyl-4-hydroxy-6-bromothiochroman obtained in the above (1), and the mixture was allowed to react at 70° C. for 4 hours. After allowed to cool, the reaction mixture was poured into an ice bath, and extracted with dichloromethane. The resultant dichloromethane layer was washed with water and with a saturated sodium chloride aqueous solution, dried over anhydrous sodium sulfate and subjected to column chromatography (silica gel; solvent hexane:ethyl acetate=20:1) to give 9.35 g (yield 87%) of 5,8-dimethyl-4-(2-fluoroethoxy)-6-bromothiochroman (corresponding to compound of the formula (VII)).

$^1$H-NMR (solvent: CDCl$_3$, internal standard: tetramethylsilane, ppm): 1.5–2.0(1H,m), 2.19(3H,s), 2.44 (3H,s), 2.5–2.9(2H,m), 3.1–3.4(1H,m), 3.5–3.8(1H,m), 3.8–4.1(1H,m), 4.30(1H,t, J=4.2 Hz), 4.68(1H,m), 4.83(1H, t, J=4.2 Hz), 7.3(1H,s)

(3) Carboxylation step

To a solution of the 9.35 g (29.3 mmol) of the 5,8-dimethyl-4-(2-fluoroethoxy)-6-bromothiochroman obtained in the above (2) and 1.48 g (60.8 mmol) of magnesium in tetrahydrofuran (THF) was added 5.43 g (49.8 mmol) of ethyl bromide, and the mixture was refluxed under heat for 2 hours. The reaction mixture was cooled to room temperature, and a carbon dioxide gas was bubbled for 1 hour. A 5% hydrochloric acid aqueous solution and ice water were poured into the reaction mixture, and the mixture was extracted with ethyl acetate. A 5% sodium carbonate aqueous solution was added to the resultant ethyl acetate layer to separate it into two phases. The resultant layer of the sodium carbonate aqueous solution was adjusted to a pH of 1 by adding concentrated hydrochloric acid. A precipitated solid was recovered by filtration, and dried to give 5.37 g (yield 64%) of 4-(2-fluoroethoxy)-5,8-dimethylthiochroman-6-carboxylic acid (corresponding to compound of the formula (II-0)).

$^1$H-NMR (solvent: CDCl$_3$, internal standard: tetramethylsilane, ppm): 1.6–2.0(1H,m), 2.26(3H,s), 2.5–2.9(3H,s), 2.64(3H,s), 3.1–3.5(1H,m), 3.5–3.8(1H,m), 3.8–4.1(1H,m), 4.32(1H,t, J=4.2 Hz), 4.7–4.9(2H,m), 7.71 (1H,s)

(4) Oxidation step 4 ml of acetic acid and 6.24 g (56.7 mmol) of a 30% hydrogen peroxide aqueous solution as an oxidizing agent were added to 5.37 g (18.9 mmol) of the 4-(2-fluoro-eth-oxy)-5,8-dimethylthiochroman-6-carboxylic acid, and the mixture was allowed to react at 80° C. for 2 hours. After the reaction mixture was allowed to cool, a 2% sodium hydrogensulfite aqueous solution was added to the reaction mixture, excessive hydrogen peroxide was removed, and a precipitated crystal was recovered by filtration and dried to give 5.08 g (yield 85%) of 4-(2-fluoroethoxy)-5,8-dimethylthiochroman-6-carboxylic acid-1,1-dioxide (corresponding to compound of the formula (II-2)).

$^1$H-NMR (solvent: CDCl$_3$, internal standard: tetramethylsilane, ppm): 2.5–2.8(2H,m), 2.61(3H,s), 2.78 (3H,s), 3.1–3.4(1H,m), 3.6–4.1(3H,m), 4.33(1H,t, J=4.1 Hz), 4.7–4.9(2H,m), 7.81(1H,s)

(REFERENTIAL PREPARATION EXAMPLE 2)

(1) Etherification step 5 ml of 2-fluoroethanol and 3 drops of concentrated sulfuric acid were added to 4.3 g (16.7 mmol) of 4-hydroxy-5-methylthiochroman-1,1-dioxide-6-carboxylic acid (corresponding to compound of the formula (XII-2), and the mixture was refluxed under heat for 17 hours. After allowed to cool, the reaction mixture was poured into an ice bath, and extracted with ethyl acetate twice. An organic layer was washed with a saturated sodium chloride aqueous solution and dried over anhydrous sodium sulfate, and the solvent was distilled off. The residue was subjected to column chromatography (silica gel; hexane: ethyl acetate=5:3) to give 1.2 g (yield 13%) of 4-(2-fluoroethoxy)-6-(2-fluoroethoxycarbonyl)-5-methylthiochroman-1,1-dioxide (corresponding to compound of the formula (XI-2)).

$^1$H-NMR (solvent: CDCl$_3$, internal standard: tetramethylsilane, ppm): 2.58(3H,s), 2.6–2.8(2H,m), 3.1–3.4(1H,m), 3.5–4.1(3H,m), 4.2–4.5(3H,m), 4.6–5.1(4H,m), 7.80(1H,d), 7.92(1H,d).

(2) Hydrolysis step 0.4 Gram of potassium hydroxide, 5 ml of ethanol and 2 ml of water were added to 1.2 g (3.3 mmol) of 4-(2-fluoroethoxy)-6-(2-fluoroethoxycarbonyl)-5-methylthiochroman-1,1-dioxide (corresponding to compound of the formula (XI-2), and the mixture was stirred under heat at 60° C. for 2 hours. After the completion of the reaction, the solvent was distilled off, 5 ml of water was added, and the mixture was adjusted to a pH of 1 by adding 2N hydrochloric acid. Thereafter, the mixture was extracted with ethyl acetate twice. An organic layer was washed with a saturated sodium chloride aqueous solution and dried over anhydrous sodium sulfate, and the solvent was distilled off to give 1.0 g (yield 100%) of 4-(2-fluoroethoxy)-5-methylthiochroman-1,1-dioxide-6-carboxylic acid (corresponding to compound of the formula (II-2)).

$^1$H-NMR (solvent: acetone-d6, internal standard: tetramethylsilane): 2.62(3H,s), 2.6–2.7(1H,m), 2.8–3.1(1H, m), 3.2–4.5(5H,m), 4.8–5.1(2H,m), 7.80(1H,d), 7.98(1H,d), 8.80(1H,bs).

(REFERENTIAL PREPARATION EXAMPLE 3)
(1) Etherification step 15 ml of 2-chloroethanol and 0.1 ml of concentrated sulfuric acid were added to 2.3 g (9.0 mmol) of 4-hydroxy-5-methylthiochroman-1,1-dioxide-6-carboxylic acid (corresponding to compound of the formula (XII-2)), and the mixture was refluxed under heat for 5 hours. After allowed to cool, the reaction mixture was poured into an ice bath, and extracted with ethyl acetate twice. An organic layer was washed with a saturated sodium chloride aqueous solution and dried over anhydrous sodium sulfate, and the solvent was distilled off. The residue was subjected to column chromatography (silica gel; hexane: ethyl acetate= 2:1) to give 0.7 g (yield 20%) of 4-(2-chloroethoxy)-6-(2-chloroethoxycarbonyl)-5-methylthiochroman-1,1-dioxide (corresponding to compound of the formula (XI-2)).

$^1$H-NMR (solvent: CDCl$_3$, internal standard: tetramethylsilane):2.61(3H,s),2.6–2.7(2H,m),3.0–3.4(1H, m), 3.5–4.0(7H,m), 4.59(2H,t), 4.76(1H,t), 7.83(1H,d), 7.96 (1H,d).

(2) Hydrolysis step 0.15 Gram of potassium hydroxide, 3 ml of ethanol and 1 ml of water were added to 0.7 g (1.8 mmol) of 4-(2-chloroethoxy)-6-(2-chloroethoxycarbonyl)-5-methylthiochroman-1,1-dioxide (corresponding to compound of the formula (XI-2)), and the mixture was stirred under heat at 60° C. for 2 hours. After the completion of the reaction, the solvent was distilled off, 5 ml of water was added, and the mixture was adjusted to a pH of 1 by adding 2N hydrochloric acid. Thereafter, the mixture was extracted with ethyl acetate twice. An organic layer was washed with a saturated sodium chloride aqueous solution and dried over anhydrous sodium sulfate, and the solvent was distilled off to give 0.6 g (yield 100%) of 4-(2-chloroethoxy)-5-methylthiochroman-1,1-dioxide-6-carboxylic acid (corresponding to compound of the formula (II-2)).

$^1$H-NMR (solvent: acetone-d6, internal standard: tetramethylsilane):2.63(3H,s),2.6–3.1(2H,m),3.2–4.2(6H, m), 4.91(1H,t), 7.79(1H,d), 7.98(1H,d)

(REFERENTIAL PREPARATION EXAMPLE 4)
(1) Alcoholation step 30 ml of methanol and 20 ml of dichloromethane were added to 7.4 g (25.6 mmol) of 5-chloro-6-ethoxycarbonyl-8-fluorothiochroman-4-one (corresponding to compound of the formula (VIII)). While the mixture was maintained at a temperature not exceeding 0° C. with a sodium chloride aqueous solution and an ice bath, 0.97 g (25.6 mmol) of sodium borohydride as a reducing agent was gradually added. The mixture was allowed to react at room temperature for 3 hours, and then the reaction mixture was poured into a 5% hydrochloric acid aqueous solution and extracted with dichloromethane. The resultant organic layer was dried over anhydrous sodium sulfate, concentrated and purified by column chromatography (silica gel; hexane:ethyl acetate= 2:1) to give 2.9 g (yield 40%) of 4-hydroxy-5-chloro-6-ethoxycarbonyl-8-flurothiochroman (corresponding to compound of the formula (IX)).

$^1$H-NMR (solvent: CDCl$_3$, internal standard: tetramethylsilane): 1.39(3H,t),1.5–2.1(1H,m),2.4–3.6(4H, m), 4.38(2H,q), 5.28(1H,m), 7.44(1H,d)

(2) Etherification step 5 ml of 2-fluoroethanol and 3 drops of concentrated sulfuric acid were added to 2.4 g (8.2 mmol) of 4-hydroxy-5-chloro-6-ethoxycarbonyl-8-flurothiochroman (corresponding to compound of the formula (IX)), and the mixture was refluxed under heat for 5 hours. After allowed to cool, the reaction mixture was poured into an ice bath, and extracted with ethyl acetate twice. An organic layer was washed with a saturated sodium chloride aqueous solution and dried over anhydrous sodium sulfate, and the solvent was distilled off to give 2.2 g (yield 79%) of 4-(2-fluoroethoxy)-5-chloro-6-ethoxycarbonyl-8-fluorothiochroman (corresponding to compound of the formula (X)).

$^1$H-NMR (solvent: CDCl$_3$, internal standard: tetramethylsilane): 1.38(3H,t),1.5–2.0(1H,m),2.5–3.0(2H, m), 3.1–4.3(6H,m), 4.82(1H,t), 5.00(1H,bs), 7.44(1H,d)

(3) Oxidation step 4 ml of acetic acid and 2.2 ml (21.7 mmol) of a 30% hydrogen peroxide aqueous solution as an oxidizing agent were added to 2.1 g (7.2 mmol) of 4-(2-fluoroethoxy)-5-chloro-6-ethoxycarbonyl-8-fluorothiochroman (corresponding to compound of the formula (X)), and the mixture was allowed to react at 80° C. for 3 hours. The reaction mixture was allowed to cool, then a 2% sodium hydrogensulfite, and excessive hydrogen peroxide was removed. The reaction mixture was extracted with ethyl acetate twice. An organic layer was washed with a saturated sodium chloride aqueous solution and then dried over anhydrous sodium sulfate to give 3.4 g (yield 100%) of a crude product of 4-(2-fluoroethoxy)-5-chloro-6-ethoxycarbonyl-8-fluorothiochroman-1,1-dioxide (corresponding to compound of the formula (XI-2)).

$^1$H-NMR (solvent: CDCl$_3$, internal standard: tetramethylsilane): 1.41(3H,t), 2.3–3.0(2H,m), 3.1–3.5(1H, m), 3.6–4.6(6H,m), 4.7–5.1(2H,m), 7.57(1H,d)

m.p. 87°–89° C.

(4) Hydrolysis step 0.77 Gram of potassium hydroxide and 15 ml of ethanol were added to 3.4 g (9.2 mmol) of 4-(2-fluoroethoxy)-5-chloro-6-ethoxycarbonyl-8-fluorothiochroman-1,1-dioxide (corresponding to compound of the formula (XI-2)), and the mixture was stirred at room temperature for 3 hours. After the completion of the reaction, the solvent was distilled off, and 5 ml of water was added. Then, the mixture was adjusted to a pH of 1 by adding 2N hydrochloric acid. Then, the mixture was extracted with ethyl acetate twice. An organic layer was washed with a saturated sodium chloride aqueous solution and dried over anhydrous sodium sulfate, and the solvent was distilled off to give 2.9 g (yield 92%) of 4-(2-fluoroethoxy)-5-chloro-8-fluorothiochroman-1,1-dioxide-6-carboxylic acid (corresponding to compound of the formula (II-2)).

$^1$H-NMR (solvent: acetone-d6, internal standard: tetramethylsilane):2.3–3.2(2H,m),3.3–4.5(5H,m),4.88(1H, t), 5.07(1H,m), 7.79(1H,d)

m.p. 163°–165° C.

(PREPARATION EXAMPLE 1)

Synthesis of 4-(2-fluoroethoxy)-5,8-dimethyl-6-(1-ethyl-5-hydroxypyrazol-4-yl)carbonylthiochroman-1,1-dioxide (Compound No. 1) (corresponding to step 1)

5.08 Grams (16.1 mmol) of the 4-(2-fluoroethoxy)-5,8-dimethylthiochroman-6-carboxylic acid-1,1-dioxide (corresponding to carboxylic acid derivative of the formula (II)) obtained in Referential Preparation Example 1 and 1.98 g (17.7 mmol) of 1-ethyl-5-hydroxypyrazole (corresponding to compound of the formula (III)) were dissolved in t-amyl alcohol. To this solution was added 3.65 g (17.7 mmol) of N,N'-dicyclohexylcarbodiimide (DCC) as a dehydrating condensation agent, and the mixture was stirred at room temperature for 2 hours. Then, 1.67 g (12.1 mmol) of anhydrous potassium carbonate as a base was added, and the mixture was allowed to react at 80° C. for 8 hours. After the completion of the reaction, the solvent was distilled under reduced pressure, and the residue was dissolved in a 3% sodium carbonate aqueous solution. An insoluble substance was removed by filtration, and the residue was further washed with ethyl acetate. The resultant aqueous layer was acidified with 5% hydrochloric acid, and a formed oily substance was extracted with ethyl acetate. The ethyl acetate was distilled off under reduced pressure to give 4.71 g (yield 71%) of the end product.

(PREPARATION EXAMPLE 2)

Synthesis of 4-(2-fluoroethoxy)-5,8-dimethyl-6-(1-ethyl-5-n-propanesulfonyloxypyrazol-4-yl) carbonylthiochroman-1,1-dioxide (Compound No. 2) (corresponding to step 2)

1.00 Gram (2.44 mmol) of the 4-(2-fluoroethoxy)-5,8-dimethyl-6-(1-ethyl-5-hydroxypyrazol-4-yl) carbonylthiochroman-1,1-dioxide (corresponding to pyrazole derivative of the formula (Ia)) obtained in Preparation Example 1 was dissolved in 10 ml of dichloromethane. To this mixture solution was added a solution of 0.67 g (4.87 mmol) of potassium carbonate as a base in 10 ml of water. 0.42 Gram (2.93 mmol) of n-propanesulfonyl chloride (corresponding to compound of the formula (IV)) as a reaction reagent was added to the mixture, and 0.05 g (0.2 mmol) of benzyltriethylammonium chloride as a phase transfer catalyst was added. The mixture was allowed to react at room temperature for 2 hours, and then, further refluxed under heat for 2 hours. After the completion of the reaction, the reaction mixture was allowed to cool, and water and dichloromethane were added to separate the reaction mixture into two phases. The resultant organic layer was consecutively washed with distilled water, with a saturated sodium hydrogencarbonate and with a sodium chloride aqueous solution, dried over anhydrous sodium sulfate, concentrated and purified by flush column chromatography to give 0.79 g (yield 63%) of the subject end product.

(PREPARATION EXAMPLE 3)

Synthesis of 4-(2-fluoroethoxy)-5 8-dimethyl-6-(1-ethyl-5-p-toluenesulfonyloxypyrazol-4-yl) carbonylthiochroman-1,1-dioxide (Compound No. 3) (corresponding to step 2)

The subject end product in an amount of 0.45 g (yield 65%) was obtained in the same manner as in Preparation Example 2 except that n-propanesulfonyl chloride (corresponding to compound of the formula (IV)) was replaced with p-toluenesulfonyl chloride.

(PREPARATION EXAMPLE 4)

Synthesis of 4-(2-fluoroethoxy)-5,8-dimethyl-6-(1-ethyl-5-cyclohexylcarbonyloxypyrazol-4-yl)-carbonylthiochroman-1,1-dioxide (Compound No. 4) (corresponding to step 2)

A solution of 0.50 g (1.22 mmol) of the 4-(2-fluoroethoxy)-5,8-dimethyl-6-(1-ethyl-5-hydroxypyrazol-4-yl)carbonylthiochroman-1,1-dioxide obtained in Preparation Example 1 and 0.16 g (0.58 mmol) of a solution of triethylamine as a base in dichloromethane was cooled to 0° C., and 0.21 g (1.46 mmol) of cyclohexylcarbonyl chloride (corresponding to compound of the formula (IV)) was dropwise added. The mixture was allowed to react at room temperature for 2 hours. After the completion of the reaction, the reaction mixture was poured into a saturated sodium hydrogencarbonate aqueous solution, and extracted with ethyl acetate. The resultant organic layer was washed with a saturated sodium chloride aqueous solution, dried over anhydrous sodium sulfate, and concentrated and purified by flush column chromatography to give 0.36 g (yield 56%) of the subject end product.

(PREPARATION EXAMPLE 5)

Synthesis of 4-(2-fluoroethoxy)-5-methyl-6-(1-ethyl-5-hydroxypyrazol-4-yl)carbonylthiochroman-1,1-dioxide (Compound No. 5) (corresponding to step 1)

1.0 Gram (3.3 mmol) of 4-(2-fluoroethoxy)-5-methylthiochroman-1,1-dioxide-6-carboxylic acid (corresponding to carboxylic acid of the formula (II)) and 0.45 g (4.0 mmol) of 1-ethyl-5-hydroxypyrazole (corresponding to compound of the formula (III)) were dissolved in t-amyl alcohol. To this solution was added 0.83 g (4.0 mmol) of N,N'-dicyclohexylcarbodiimide (DCC) as a dehydrating condensation agent, and the mixture was stirred at room temperature for 2 hours. Then, 0.34 g (2.5 mmol) of anhydrous potassium carbonate as a base was added, and the mixture was allowed to react at 80° C. for 8 hours. After the completion of the reaction, the solvent was distilled under reduced pressure, and the residue was dissolved in a 3% sodium carbonate aqueous solution. An insoluble substance was removed by filtration, and the residue was further washed with ethyl acetate. The resultant aqueous layer was acidified with 5% hydrochloric acid, and a formed oily substance was extracted with ethyl acetate. The ethyl acetate was distilled off under reduced pressure to give 1.2 g (yield 90%) of the subject end product.

(PREPARATION EXAMPLE 6)

Synthesis of 4-(2-fluoroethoxy)-5-methyl-6-(1-ethyl-5-n-propanesulfonyloxypyrazol-4-yl) carbonylthiochroman-1,1-dioxide (Compound No. 6) (corresponding to step 2)

0.63 Gram (1.6 mmol) of the 4-(2-fluoroethoxy)-5-methyl-6-(1-ethyl-5-hydroxypyrazol-4-yl)-carbonylthiochroman-1,1-dioxide (corresponding to pyrazole derivative of the formula (Ia)) obtained in Preparation Example 5 was dissolved in 5 ml of dichloromethane. A solution of 0.4 g (3.2 mmol) of potassium carbonate as a base in 5 ml of water was added. To this mixture solution was added 0.4 ml (3.2 mmol) of n-propanesulfonyl chloride as a reaction reagent, and further, 0.05 g (0.2 mmol) of benzyltriethyl-ammonium chloride as a phase transfer catalyst was added. The mixture was allowed to react at room temperature for 1 day. After the completion of the reaction, water and dichloromethane were added to separate the reaction mixture into two phases. The resultant organic layer was consecutively washed with distilled water, with a saturated sodium hydrogencarbonate aqueous solution and with a saturated sodium chloride aqueous solution, dried over anhydrous sodium sulfate, concentrated and purified by column chromatography (silica gel; hexane:ethyl acetate=1:1) to give 0.55 g (yield 68%) of the subject end product.

(PREPARATION EXAMPLE 7)

Synthesis of 4-(2-chloroethoxy)-5-methyl-6-(l-ethyl-5-hydroxypyrazol-4-yl)carbonylthiochroman-1,1-dioxide (Compound No. 7) (corresponding to step 1)

0.6 Gram (1.9 mmol) of 4-(2-chloroethoxy)-5-methylthiochroman-1,1-dioxide-6-carboxylic acid (corresponding to carboxylic acid of the formula (II)) and 0.24 g (2.1 mmol) of 1-ethyl-5-hydroxypyrazole (corresponding to compound of the formula (III)) were dissolved in t-amyl alcohol. To this solution was added 0.39 g (2.1 mmol) of N,N'-dicyclohexylcarbodiimide as a dehydrating condensation agent, and the mixture was stirred at room temperature for 2 hours. Then, 0.20 g (1.4 mmol) of anhydrous potassium carbonate was added, and the mixture was allowed to react at 80° C. for 8 hours. After the completion of the reaction, the solvent was distilled off under reduced pressure, and the residue was dissolved in a 3% sodium carbonate aqueous solution. An insoluble substance was removed by filtration, and the residue was washed with ethyl acetate. The resultant aqueous layer was acidified with 5% hydrochloric acid, and a formed oily substance was extracted with ethyl acetate. The ethyl acetate was distilled off under reduced pressure to give 0.34 g (yield 43%) of the subject end product.

(PREPARATION EXAMPLE 8)

Synthesis of 4-(2-chloroethoxy)-5-methyl-6-(1-ethyl-5-n-propanesulfonyloxypyrazol-4-yl)carbonylthiochroman-1,1-dioxide (Compound No. 8) (corresponding to step 2)

0.34 Gram (0.8 mmol) of the 4-(2-chloroethoxy)-5-methyl-6-(1-ethyl-5-hydroxypyrazol-4-yl)-carbonylthiochroman-1,1-dioxide (corresponding to pyrazole derivative of the formula (Ia)) obtained in Preparation Example 7 was dissolved in 3 ml of dichloromethane, and a solution of 0.23 g (1.6 mmol) of potassium carbonate as a base in 2 ml of water was added. To this mixture was added 0.2 ml (1.6 mmol) of n-propanesulfonyl chloride (corresponding to compound of the formula (IV)) as a reaction reagent, and 0.01 g (0.05 mmol) of benzyltriethylammonium chloride as a phase transfer catalyst was added. The mixture was allowed to react at room temperature for 1 day. After the completion of the reaction, water and dichloromethane were added to separate the reaction mixture to two phases. The resultant organic layer was consecutively washed with distilled water, with a saturated sodium hydrogencarbonate and with a saturated sodium chloride aqueous solution, then dried over anhydrous sodium sulfate, concentrated and purified by column chromatography (silica gel; hexane:ethyl acetate=1:1) to give 0.23 g (yield 54%) of the subject end product.

(PREPARATION EXAMPLE 9)

Synthesis of 4-(2-fluoroethoxy)-5-chloro-6-(1-ethyl-5-hydroxypyrazol-4-yl)carbonyl-8-fluorothiochroman-1,1-dioxide (Compound No. 9) (corresponding to step 1)

1.5 Gram (4.3 mmol) of 4-(2-fluoroethoxy)-5-chloro-8-fluorothiochroman-1,1-dioxide-6-carboxylic acid (corresponding to carboxylic acid of the formula (II)) and 0.53 g (4.7 mmol) of 1-ethyl-5-hydroxypyrazole (corresponding to compound of the formula (III)) were dissolved in 4 ml of t-amyl alcohol. To this solution was added 0.97 g (4.7 mmol) of N,N'-dicyclohexylcarbodiimide as a dehydrating condensation agent, and the mixture was stirred at room temperature for 2 hours. Then, 0.45 g (3.2 mmol) of anhydrous potassium carbonate was added, and the mixture was allowed to react at 80° C. for 8 hours. After the completion of the reaction, the solvent was distilled off under reduced pressure, and the residue was dissolved in a 3% sodium carbonate aqueous solution. An insoluble substance was removed by filtration, and the residue was washed with ethyl acetate. The resultant aqueous layer was acidified with 5% hydrochloric acid, and a formed oily substance was extracted with ethyl acetate. The ethyl acetate was distilled off under reduced pressure to give 0.90 g (yield 48%) of the subject end product.

(PREPARATION EXAMPLE 10)

Synthesis of 4-(2-fluoroethoxy)-5-chloro-6-(1-ethyl-5-n-propanesulfonyloxypyrazol-4-yl)carbonyl-8-fluorothiochroman-1,1-dioxide (Compound No. 10) (corresponding to step 2)

0.69 Gram (1.6 mmol) of the 4-(2-fluoroethoxy)-5-chloro-6-(1-ethyl-5-hydroxypyrazol-4-yl)carbonyl-8-fluorothiochroman-1,1-dioxide (corresponding to pyrazole derivative of the formula (Ia)) obtained in Preparation Example 9 was dissolved in 5 ml of dichloromethane, and a solution of 0.26 g (1.9 mmol) of potassium carbonate as a base in 2 ml of water was added. To this mixture was added 0.21 ml (1.9 mmol) of n-propanesulfonyl chloride (corresponding to compound of the formula (IV)) as a reaction reagent, and 0.05 g (0.2 mmol) of benzyltriethylammonium chloride as a phase transfer catalyst was added. The mixture was allowed to react at room temperature for 1 day. After the completion of the reaction, water and dichloromethane were added to separate the reaction mixture to two phases. The resultant organic layer was consecutively washed with distilled water, with a saturated sodium hydrogencarbonate and with a saturated sodium chloride aqueous solution, then dried over anhydrous sodium sulfate, concentrated and purified by column chromatography (silica gel; hexane:ethyl acetate=1:1) to give 0.52 g (yield 60%) of the subject end product.

Tables 1 to 4 show the structures and physical property values of the compounds obtained in Preparation Examples 1 to 10.

TABLE 1

| Comp'd No. | Structural formula | IR(cm⁻¹) KBr tablet | ¹H-NMR (ppm) Int. Standard: tetramethylsilane Solvent: deutero chloroform | Melting point |
|---|---|---|---|---|
| (1) | | | 1.45(3H, t)2.35(3H, s)<br>2.5–2.8(2H, m)2.75(3H, s)<br>3.1–3.4(1H, m)3.6–4.4(6H, m)<br>4.6–4.9(2H, m)7.2(1H, s)<br>7.3(1H, s) | 84–88° C. |
| (2) | | 2980<br>1660<br>1300<br>1120 | 1.17(1H, t, J=7.4Hz)1.51(1H, t, J=7.3Hz)<br>1.8–2.3(3H, m)2.33(3H, S)<br>2.5–2.8(2H, m)2.76(3H, s)<br>3.1–3.4(1H, m)3.5–3.8(3H, m)<br>3.9–4.1(2H, m)4.22(1H, q, J=7.3Hz)<br>4.30(1H, t, J=4.3Hz)4.67(1H, m)<br>4.83(1H, t, J=4.3Hz)7.24(1H, s)<br>7.49(1H, s) | 69–74° C. |
| (3) | | 2950<br>1670<br>1300<br>1130 | 1.51(3H, t, J=7.2Hz)2.30(3H, s)<br>2.46(3H, s)2.69(3H, s)<br>3.1–3.4(1H, m)3.6–4.4(5H, m)<br>4.20(2H,, q, J=7.2Hz)4.6–4.7(1H, m)<br>4.83(1H, t, J=4.0Hz)<br>7.07((1H, s)7.34(1H, s)<br>7.49(2H, d, J=8.3Hz)<br>7.84(2H, d, J=8.3Hz) | 84–87° C. |

TABLE 2

| Comp'd No. | Structural formula | IR(cm⁻¹) KBr tablet | ¹H-NMR (ppm) Int. Standard: tetramethylsilane Solvent: deutero chloroform | Melting point |
|---|---|---|---|---|
| (4) | | 2950<br>1780<br>1660<br>1300<br>1125 | 1.2–2.1(11H, m)1.42(3H, t, J=7.3Hz)<br>2.29(3H, s)2.4–2.8(2H, m)<br>2.74(3H, s)3.1–3.4(1H, m)<br>3.6–4.1(3H, m)3.98(2H, q, J=7.3Hz)<br>4.30(1H, t, J=4.0Hz)4.67(1H, t)<br>4.83(1H, t, J=4.0Hz)7.20(1H, s)<br>7.64(1H, s) | 75–78° C. |

TABLE 3

| Comp'd No. | Structural formula | IR(cm$^{-1}$) KBr tablet | $^1$H-NMR (ppm) Int. standard: tetramethylsilane | Melting point |
|---|---|---|---|---|
| (5) | (pyrazole with N-ethyl, OH; C(=O) linker; aryl with CH$_3$, OCH$_2$CH$_2$F, SO$_2$-containing ring) | 3400 2930 1620 1520 1300 1120 | Solvent; acetone-d6 1.39(3H, t)2.45(3H, s) 2.5–2.7(1H, m)2.8–4.5(8H, m) 4.8–5.0(2H, m)7.39(1H, s) 7.65(1H, d) 7.84(1H, d) | Glass-like substance |
| (6) | (pyrazole with N-ethyl, O-SO$_2$Pr; C(=O) linker; aryl with CH$_3$, OCH$_2$CH$_2$F, SO$_2$ ring) | 3000 1660 1560 1480 1250 1170 1130 1100 | Solvent; CDCl$_3$ 1.16(3H, t)1.51(3H, t) 1.8–2.3(2H, m)3.1–3.4(1H, m) 3.5–4.4(8H, m)4.6–5.0(2H, m) 7.48(1H, s)7.51(1H, d) 7.88(1H, d) | 129–131° C. |
| (7) | (pyrazole with N-ethyl, OH; C(=O) linker; aryl with CH$_3$, OCH$_2$CH$_2$Cl, SO$_2$ ring) | 3450 2950 1630 1540 1310 1130 | Solvent; acetone-d6 1.45(3H, t)2.46(3H, s)2.6–2.9 (2H, m)3.1–3.4(1H, m) 3.5–4.3(7H, m)4.75(1H, bs) 7.32(1H, s)7.58(1H, d) 7.91(1H, d)8.60(1H, bs) | Oily substance |

TABLE 4

| Conp'd No. | Structural formula | IR(cm$^{-1}$) KBr tablet | $^1$H-NMR (ppm) Int. Standard: tetramethylsilane | Melting point |
|---|---|---|---|---|
| (8) | (pyrazole with N-ethyl, O-SO$_2$Pr; C(=O) linker; aryl with CH$_3$, OCH$_2$CH$_2$Cl, SO$_2$ ring) | 2950 1730 1650 1540 1360 1280 1160 | Solvent; CDCl$_3$ 1.13(3H, t)1.47(3H, t) 1.8–2.2(2H, m)2.36(3H, s) 2.7–2.9(2H, m)3.1–3.4(1H, m) 3.4–4.4(9H, m)4.70(1H, bs) 7.45(1H, d)7.46(1H, s) 7.86(1H, d) | Oily substance |
| (9) | (pyrazole with N-ethyl, OH; C(=O) linker; aryl with Cl, OCH$_2$CH$_2$F, F, SO$_2$ ring) | 2950 1670 1330 1190 | Solvent; acetone-d6 1.39(3H, t)2.3–3.2(2H, m) 3.3–4.5(7H, m)4.88(1H, t) 5.04(1H, m)6.90(1H, bs) 7.50(1H, s)7.59(1H, d) | 219–222° C. |

TABLE 4-continued

| Conp'd No. | Structural formula | IR(cm$^{-1}$) KBr tablet | $^1$H-NMR (ppm) Int. Standard: tetramethylsilane | Melting point |
|---|---|---|---|---|
| (10) | 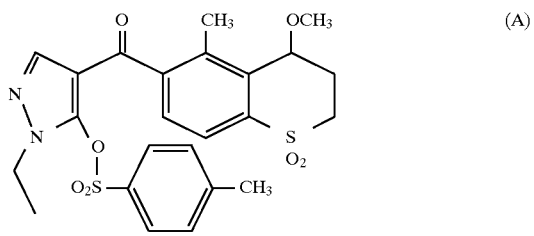 | 3000 1670 1540 1320 1180 | Solvent; CDCl$_3$ 1.19(3H, t)1.52(3H, t)1.9–2.4 (2H, m)2.5–2.9(2H, m) 3.1–3.5(1H, m)3.6–4.5(8H, m) 4.7–5.0(2H, m)7.28(1H, d) 7.47(1H, s) | 123– 126° C. |

(HERBICIDE EXAMPLES)

(1) Preparation of herbicide

97 Parts by weight of talc (trade name: Zeaklite) as a carrier, 1.5 parts by weight of alkylarylsulfonic acid (trade name: Neoplex, supplied by Kao-Atlas K.K.) as a surfactant and 1.5 parts by weight of a mixture of nonionic and anionic surfactants (trade name: Sorpol 800A, supplied by Toho Chemical Co., Ltd.) were uniformly pulverized and mixed to prepare a carrier for a wettable powder.

90 Parts by weight of the above carrier and 10 parts by weight of one of the compounds obtained in the above Preparation Examples (or 10 parts by weight of the following compound (A) for Comparative Example)were uniformly pulverized and mixed to obtain herbicides.

The compound (A) used as a comparative chemical has the following structure.

The usefulness of the compound of the present invention as a herbicide will be specifically explained with reference to the following tests.

(2) Biological test (Foliar treatment test)

Seeds of large crabgrass, barnyardgrass, green foxtail, cocklebur, velvetleaf and slender amaranth and seeds of corn, wheat and barley were sown in 1/5,000-are Wagner pots filled with upland soil, and covered with upland soil. Then, the seeds were grown in a greenhouse. When these plants were at their there and four-leaved stage, a predetermined amount of the herbicide obtained in the above (1) was suspended in water and uniformly sprayed to their leaves and stalks at a dosage of 2,000 liters/hectare. Thereafter, the plants were grown in the greenhouse, and 30 days after the treatment, the herbicide was evaluated for herbicidal efficacy and phytotoxicity to the crops. Table 5 (No. 1) and (No. 2) show the results.

The herbicidal efficacy and the phytotoxicity to the crops are shown as follows.

(Ratings)

| | Ratio of remaining plant weight to non-treated (%) |
|---|---|
| Herbicidal efficacy | |
| 0 | 81–100 |
| 1 | 61–80 |
| 2 | 41–60 |
| 3 | 21–40 |
| 4 | 1–20 |
| 5 | 0 |
| Phytotoxicity to crops | |
| − | 100 |
| ± | 95–99 |
| + | 90–94 |
| ++ | 80–89 |
| +++ | 0–79 |

The ratio of remaining plant weight to non-treated was determined as a ratio of remaining plant weight to non-treated=(remaining plant weight in treated plot/remaining plant weight in non-treated plot)×100.

TABLE 5

| Compound No. | Dosage (g$^{a.i.}$/ hectare) | Herbicidal efficacy | | | | | | Phytotoxicity | | |
|---|---|---|---|---|---|---|---|---|---|---|
| | | large crabgrass | barnyard grass | green foxtail | cocklebur | velvet- leaf | slender amaranth | corn | wheat | barley |
| (No. 1) | | | | | | | | | | |
| (1) | 300 | 5 | 5 | 5 | 5 | 5 | 5 | — | — | — |
| (2) | 300 | 5 | 5 | 5 | 5 | 5 | 5 | — | — | — |
| (3) | 300 | 5 | 5 | 5 | 5 | 5 | 5 | — | — | — |
| (4) | 300 | 5 | 4 | 5 | 5 | 5 | 5 | — | — | — |
| (A) | 300 | 5 | 5 | 5 | 5 | 5 | 5 | ++ | ± | + |

TABLE 5-continued

| Compound No. used | Dosage (g^a.i./ hectare) | Herbicidal efficacy | | | | | Phytotoxicity | | |
|---|---|---|---|---|---|---|---|---|---|
| | | large crabgrass | barnyard grass | green foxtail | cocklebur | velvet- leaf | slender amaranth | corn | wheat | barley |

| | | | | (No. 2) | | | | | | |
| (5) | 300 | 5 | 5 | 5 | 5 | 5 | 5 | — | — | — |
| (6) | 300 | 4 | 5 | 4 | 5 | 5 | 5 | — | — | — |
| (7) | 300 | 5 | 5 | 5 | 5 | 5 | n.d. | — | — | — |
| (8) | 300 | 5 | 5 | 4 | 5 | 4 | 4 | — | — | — |
| (9) | 300 | 5 | 4 | 4 | 5 | 4 | 5 | — | — | — |
| (10) | 300 | 5 | 5 | 4 | 5 | 4 | 4 | — | — | — |
| (A) | 300 | 5 | 5 | 5 | 5 | 5 | 5 | ++ | ± | + | a.i. = abbreviation for "active ingredient"
n.d. = abbreviation for "not detected"

The results in Table 5 (No. 1) and (No. 2) show the following. In the foliar treatment at a three- and four-leaved stage, the comparative herbicide causes phytotoxicity on crops, while all the herbicides of the present invention are free from phytotoxicity to the crops and have high safety to the crops. Further, the herbicides of the present invention exhibit excellent herbicidal efficacy to various weeds and show excellent selectivity between crops and weeds.

(3) Biological test (Soil treatment test)

Seeds of weeds such as large crabgrass, barnyardgrass, green foxtail, cocklebur, velvetleaf and slender amaranth and seeds of corn, wheat, barley and cotton were sown in 1/5,000-are Wagner pots filled with upland soil, and covered with upland soil. Then, a predetermined amount of the herbicide prepared in the above (1) was suspended in water and uniformly sprayed onto the soil surface at 2,000 liters/hectare. Thereafter, the seeds were grown in a greenhouse, and 20 days after the treatment, the herbicide was determined for herbicidal efficacy and phytotoxicity to crops. Table 6 shows the results.

As explained above, according to the present invention, there are provided novel pyrazole derivatives which remarkably excellent selectivity between crops and weeds in foliar treatment and soil treatment, and herbicides containing them as active ingredients.

What is claimed is:

1. A pyrazole derivative of the formula (I),

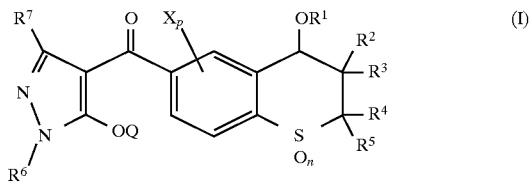

wherein:
$R^1$ is a $C_1$~$C_6$ haloalkyl group having at least one halogen atom;
each of $R^2$, $R^3$, $R^4$ and $R^5$ is independently a hydrogen atom or a $C_1$~$C_4$ alkyl group;

TABLE 6

| Compound No. used | Dosage (g^a.i./ hectare) | Herbicidal efficacy | | | | | | Phytotoxicity | | | |
|---|---|---|---|---|---|---|---|---|---|---|---|
| | | large crabgrass | barnyard grass | green foxtail | cocklebur | velvet- leaf | slender amaranth | corn | wheat | barley | cotton |
| (1) | 300 | 5 | 5 | 4 | 5 | 5 | 4 | — | — | — | — |
| (2) | 300 | 5 | 5 | 5 | 5 | 5 | 5 | — | — | ± | — |
| (3) | 300 | 5 | 5 | 5 | 5 | 5 | 5 | — | — | — | — |
| (4) | 300 | 5 | 5 | 4 | 4 | 5 | 5 | — | — | — | — |
| (5) | 300 | 5 | 5 | 5 | 5 | 5 | 5 | — | — | — | — |
| (6) | 300 | 5 | 5 | 5 | 5 | 5 | 4 | — | — | — | — |
| (7) | 300 | 5 | 5 | 3 | 5 | 5 | 5 | — | — | — | — |
| (8) | 300 | 5 | 4 | 4 | 5 | 5 | 5 | — | — | — | — |
| (9) | 300 | 5 | 5 | 5 | 5 | 5 | 4 | — | — | — | — |
| (10) | 300 | 5 | 5 | 5 | 4 | 5 | 3 | — | — | — | — |
| (A) | 300 | 5 | 5 | 5 | 5 | 5 | 5 | — | — | ± | +++ | a.i. = abbreviation for "active ingredient"

The results in Table show the following. In the soil treatment test, the comparative herbicide causes phytotoxicity on crops, while all the herbicides of the present invention are free from phytotoxicity to the crops and have high safety to the crops. Further, it is seen that the herbicides of the present invention exhibit excellent herbicidal efficacy to various weeds and show excellent selectivity between crops and weeds.

$R^6$ is a $C_1$~$C_4$ alkyl group,
$R^7$ is a hydrogen atom or a $C_1$~$C_4$ alkyl group,
X is a $C_1$~$C_4$ alkyl group or a halogen atom, each of p and n is independently an integer of 0, 1 or 2; and
Q is a hydrogen atom or a group of -A-B, in which A is $-SO_2-$, $-(CH_2)k\text{-}CO-$ or $-CR^8R^9-$ in which k is an integer of 0 or 1 to 3 and each of $R^8$ and $R^9$ is independently a hydrogen atom or a $C_1 \sim C_4$ alkyl group; and B is a $C_1 \sim C_{12}$ alkyl group, a $C_3 \sim C_{12}$ cycloalkyl group or a group of $-Ph\text{-}Y_m$ in which Ph is a phenyl group, Y substituted on the Ph is a $C_1 \sim C_4$ alkyl group, a $C_1 \sim C_4$ alkoxy group, a $C_1 \sim C_4$ haloalkyl group having at least one halogen atom, a nitro group or a halogen atom, and m is an integer of 0 or 1 to 2.

2. The pyrazole derivative of claim 1, wherein $R^1$ is a linear or branched $C_1 \sim C_4$ haloalkyl group.

3. The pyrazole derivative of claim 2, wherein $R^1$ is 2-chloroethyl or 2-fluoroethyl.

4. The pyrazole derivative of claim 1, wherein each of $R^2$, $R^3$, $R^4$ and $R^5$ is independently a hydrogen atom or methyl.

5. The pyrazole derivative of claim 1, wherein $R^6$ is methyl or ethyl.

6. The pyrazole derivative of claim 1, wherein $R^7$ is a hydrogen atom or methyl.

7. The pyrazole derivative of claim 1, wherein X is methyl, a chlorine atom or a fluorine atom.

8. The pyrazole derivative of claim 7, wherein X(s) is/are substituted on the 5-position and/or the 8-position on the thiochroman ring.

9. The pyrazole derivative of claim 1, wherein n is 2.

10. The pyrazole derivative of claim 1, wherein Q is a hydrogen atom.

11. The pyrazole derivative of claim 1, wherein Q is a group of -A-B in which A is $-SO_2-$ or $-(CH_2)k\text{-}CO-$ and B is a $C_1 \sim C_4$ alkyl group, a $C_3 \sim C_8$ cycloalkyl group or a group of $Ph\text{-}Y_m$ in which Ph is phenyl, Y substituted on Ph is a $C_1 \sim C_4$ alkyl group, a $C_1 \sim C_4$ alkoxy group, a $C_1 \sim C_4$ haloalkyl group having at least 1 halogen atom, a nitro group or a halogen atom, and m is an integer of 0 or 1 to 2.

12. The pyrazole derivative of claim 11, wherein Q is a group of -A-B in which A is $-SO_2-$ and B is ethyl, n-propyl or toluyl (Y is 4-methyl and m is 1 in -Ph-$Y_m$) or in which A is $-CO-$ or $-CH_2CO-$, k is 0 or 1 in $-(CH_2)_k\text{-}CO-$, and B is cyclohexyl or phenyl (m=0 in $-Ph\text{-}Y_m$).

13. A herbicide comprising the pyrazole derivative of claim 1 as an active ingredient and a herbicidal carrier.

14. A herbicide comprising the pyrazole derivative of claim 2 as an active ingredient and a herbicidal carrier.

15. A herbicide comprising the pyrazole derivative of claim 3 as an active ingredient and a herbicidal carrier.

16. A herbicide comprising the pyrazole derivative of claim 4 as an active ingredient and a herbicidal carrier.

17. A herbicide comprising the pyrazole derivative of claim 5 as an active ingredient and a herbicidal carrier.

18. A herbicide comprising the pyrazole derivative of claim 6 as an active ingredient and a herbicidal carrier.

19. A herbicide comprising the pyrazole derivative of claim 7 as an active ingredient and a herbicidal carrier.

20. A herbicide comprising the pyrazole derivative of claim 8 as an active ingredient and a herbicidal carrier.

21. A herbicide comprising the pyrazole derivative of claim 9 as an active ingredient and a herbicidal carrier.

22. A herbicide comprising the pyrazole derivative of claim 10 as an active ingredient and a herbicidal carrier.

23. A herbicide comprising the pyrazole derivative of claim 11 as an active ingredient and a herbicidal carrier.

24. A herbicide comprising the pyrazole derivative of claim 12 as an active ingredient and a herbicidal carrier.

* * * * *